United States Patent
Baldauf

(10) Patent No.: US 7,501,361 B2
(45) Date of Patent: Mar. 10, 2009

(54) LAMINATE MATERIAL FOR AN ELASTIC DIAPER CLOSURE AND METHOD FOR ITS PRODUCTION

(75) Inventor: Georg Baldauf, Laer (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 4 days.

(21) Appl. No.: 11/008,704

(22) Filed: Dec. 9, 2004

(65) Prior Publication Data

US 2005/0130543 A1 Jun. 16, 2005

(30) Foreign Application Priority Data

Dec. 13, 2003 (DE) ............................... 103 58 409

(51) Int. Cl.
*B32B 27/12* (2006.01)
*B32B 3/06* (2006.01)
*D04H 1/00* (2006.01)
*D04H 3/00* (2006.01)

(52) U.S. Cl. .................. 442/329; 442/328; 442/364; 442/394; 442/398; 428/99

(58) Field of Classification Search .............. 442/328, 442/329, 394, 398, 399

See application file for complete search history.

(56) References Cited

U.S. PATENT DOCUMENTS

| 4,879,170 | A | * | 11/1989 | Radwanski et al. | 442/329 |
| 2003/0125707 | A1 | * | 7/2003 | Popp et al. | 604/391 |
| 2004/0020579 | A1 | * | 2/2004 | Durrance et al. | 156/66 |
| 2005/0106980 | A1 | * | 5/2005 | Abed et al. | 442/395 |

FOREIGN PATENT DOCUMENTS

| DE | 102 12 842 | 10/2003 |
| EP | 0 809 992 | 11/1996 |
| JP | 09294772 A | * 11/1997 |

OTHER PUBLICATIONS

JP 09-294772 A JPO English Translation.*

* cited by examiner

*Primary Examiner*—Jenna-Leigh Johnson
(74) *Attorney, Agent, or Firm*—Collard & Roe, P.C.

(57) ABSTRACT

A laminate material for an elastic diaper closure consists of an elastic carrier film that has a preferred elongation direction, and at least one cover layer that is laminated on the carrier film. The cover layer consists of a fiber non-woven fabric, which contains fibers of an elastic polymer and fiber components of a non-elastic thermoplastic polymer, which have been stretched in the preferred elongation direction by means of an elongation of the fiber non-woven fabric. There is also a method for making the laminate material.

3 Claims, 3 Drawing Sheets

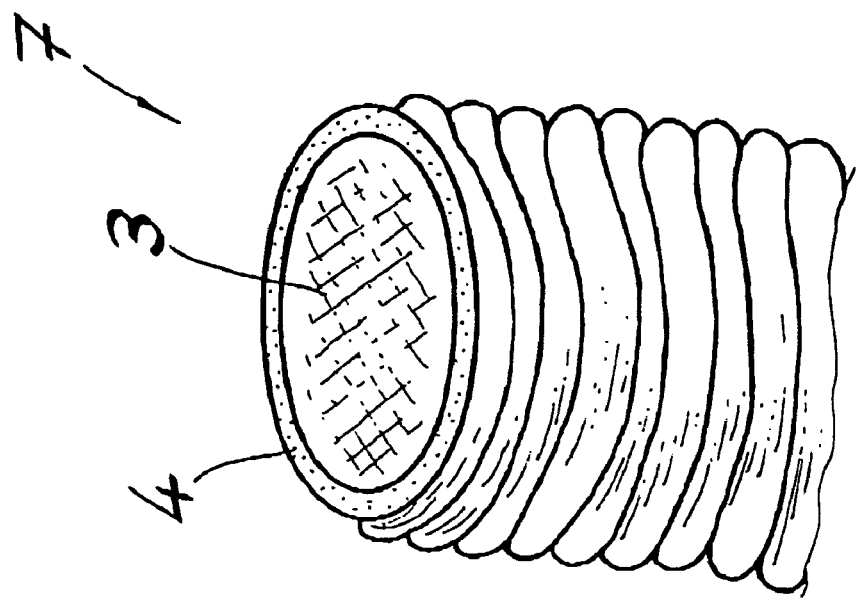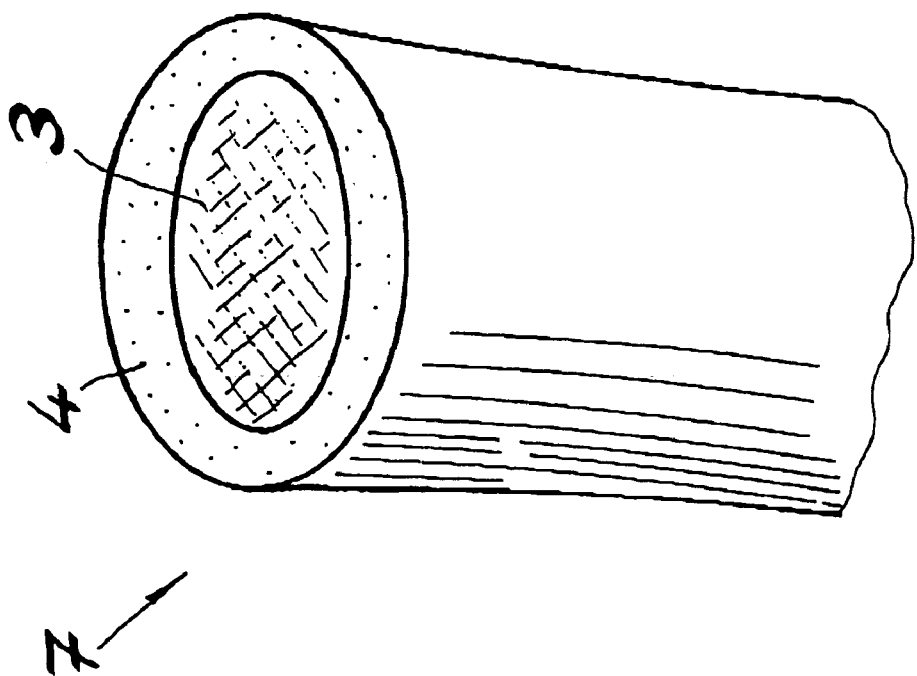

LAMINATE MATERIAL FOR AN ELASTIC DIAPER CLOSURE AND METHOD FOR ITS PRODUCTION

BACKGROUND OF THE INVENTION

1. Field of the Invention

The invention relates to a laminate material, particularly for elastic diaper closures.

2. The Prior Art

Diapers often possess mechanical hook and loop closures, which can be easily closed and opened again. Part of the hook and loop closure is provided with female closure elements, and glued onto the diaper in the front waistband region. A related hook tape with male closure elements is affixed to closure tabs that are attached on the back waistband region of the diaper, on the right and left, in each instance, and generally consist of an elastic material. When the diaper closure is being closed, and when the diaper is being worn, the elastic closure tabs are sometimes over-stretched. The over-stretching is connected with permanent elongation of the elastic material and has a disadvantageous effect on the fit of the diaper.

An elastic closure tape for diaper closures that has a plastically deformable region in the form of a moisture-permeable film and several stretchable regions is described in European Patent No. EP 0 809 992 B1. The stretchable regions alternate with the plastically deformable regions, in the direction of the width of the tape, and are made available in the shape of a line, a strip, or a spiral.

In German Patent No. DE 102 12 842 A1, a non-woven fabric material having elastic properties is described, which contains fibers of an elastic polymer and fiber components of a non-elastic thermoplastic polymer. The elastic polymer can be used, among other things, as a waistband for diapers. Diaper closures are frequently stretched by more than twice their original length in use, and are subjected to significantly greater elongation than the waistband of a diaper. For uses in which very great elongation is required, the non-woven fabric material as such therefore does not appear to be suitable.

SUMMARY OF THE INVENTION

In view of the background described above, it is an object of the invention to provide an elastic laminate material that is suitable for elastic diaper closures, in which over-stretching due to improper use, or stresses during use as intended, is largely prevented.

This object is accomplished, according to the invention, by a laminate material consisting of an elastic carrier film that has a preferred elongation direction, and at least one cover layer that is laminated on. The cover layer consists of a fiber non-woven fabric, which contains fibers of an elastic polymer and fiber components of a non-elastic thermoplastic polymer, which have been stretched in the preferred elongation direction by means of an elongation of the fiber non-woven fabric.

The laminate material according to the invention has a clearly perceivable elongation limit. The laminate material can be stretched to this limit with little force. In the elongation range up to this limit, the laminate material elastically returns to its original shape when the stress is relieved. When the laminate material is used as a diaper closure tab, this range is perceived as an elastic working range. When the elongation limit established by the material is reached, a great increase in the force required for further stretching is noticed, and the diaper closure behaves in non-elastic manner above the defined elongation limit. This has an advantageous effect on the fit of the diaper. Because of the elasticity of the diaper closure tab, the diaper closure can be appropriately stretched, in keeping with the movements of the person, and can relax again. In this connection, the diaper closure is not over-stretched, because of the elongation limit that exists, so that the fit of the diaper is maintained during its use. Male closure elements can be attached to the laminate material, cut to the form of a diaper closure tab, in the form of a hook tape, by means of gluing or bonding, for example by ultrasound.

The elasticity of the laminate material, which determines the required force during elongation, i.e. the elastic recovery force, is predetermined by the properties of the carrier film. The percentage lengthening of the laminate material until it reaches the elongation limit is established by the prior stretching of the non-elastic fiber components of the cover layer.

The carrier film is preferably a film having a thermoplastic elastomer, produced according to the film-casting or film-blowing method. Polymer mixtures suitable for this include polyurethanes, SBS, SIS, or SEBS polymers, low-density polyethylenes, or mixtures of these polymers as the elastic component. On the basis of the lengthwise orientation of the polymers during the extrusion process, the carrier film is preferably elastic in the crosswise direction. The carrier film can also contain cross-linked elastomers, such as NBR or EPDM, for example.

The fiber non-woven fabric can consist of a fiber mixture of elastic fibers and fibers of a non-elastic thermoplastic polymer. Preferably, the cover layer consists of a spun-bonded fabric, the filaments of which have a filament core of a thermoplastic elastomer and a filament mantle of a non-elastic thermoplastic polymer. In this connection, the individual filaments are structured as a so-called bi-component fiber. Suitable fiber mixtures for the elastomer filament core include, for example, polyurethanes, SIS, SBS or SEBS polymers or mixtures of these polymers, as the elastic component. The non-elastic filament mantle can consist of polypropylene or polyethylene, for example. The spun-bonded fabric is produced from endless filaments that are drawn from spinning jets by means of an air stream, utilizing the Venturi effect, and laid down onto a spinning belt in a whirled position. The fiber non-woven fabric is consolidated, by a calander, under the influence of heat and pressure, by means of needling, hot-air consolidation, or other methods known to a person skilled in the art for consolidation of non-woven fabrics.

Subsequent crosswise stretching of the consolidated fiber non-woven fabric results in cold-stretching of the non-elastic fiber components. If the fiber non-woven fabric has bi-component fibers that have an elastic core and a mantle of a non-elastic thermoplastic polymer, cold-stretching of the mantle polymer of the bi-component fibers occurs when the consolidated fiber non-woven fabric is stretched crosswise. The layer of the mantle polymer is oriented in the fiber direction, whereby the mantle polymer, which is partially oriented up to the tear limit, assures a steep increase in the tear force values of the bi-component fibers. After crosswise stretching, the fiber non-woven fabric elastically returns to its original condition, under the effect of the elastic core of the bi-component fibers. Because of the pre-stretching as described, an elastic fiber non-woven fabric having a defined elongation limit is produced, which can be elastically stretched up to a clearly perceivable elongation limit. The fiber non-woven fabric, modified by means of pre-stretching, is relaxed after its elastic recovery, and laminated onto the carrier film, which is also elastic in the crosswise direction, on one or both sides.

It is practical if the cover layer of the laminate material according to the invention has a weight per surface area unit between $10 \, g/m^2$ and $200 \, g/m^2$. A weight per surface area unit between 10 g/m² and 30 g/m² is particularly preferred. The individual fibers preferably possess a diameter between 10 μm and 30 μm. According to a preferred embodiment of the invention, the non-elastic fiber component within the fiber mixture amounts to as much as 60 wt.-%, particularly preferably approximately 20 wt.-%.

The elastic carrier film preferably has a weight per surface area unit between 5 g/m² and 150 g/m². It can consist of a multi-layer co-extrusion film that has a core of a thermoplastic elastomer and an adhesion-imparting layer for improving the adhesion of the adjacent cover layer, disposed on one or both sides. It is practical if the adhesion-imparting layer possesses a high affinity for lamination adhesives. The thickness of the co-extrusion film preferably amounts to 50 μm to 150 μm, with a thickness ratio, in the case of a three-layer structure, of 1:10:1 to 1:30:1. All of the layers of the co-extrusion film can consist of elastic thermoplastic polymers. The adhesion-imparting layer can be modified by means of additives, so that the carrier film is not blocked and has a particularly good affinity for lamination adhesives. Mineral fillers as well as mixtures of SIS, SBS, SEBS, and PU polymers with polyolefins, such as polyethylene, polypropylene, EVA, and EBA, for example, can be used as materials for the layers of the co-extrusion film. The adhesion-imparting layer can furthermore consist of a purely polyolefin material. However, it also lies within the scope of the invention that mono-films or co-extruded films are used in layer ratios other than those indicated.

The carrier film and the cover layer are preferably connected by means of an elastic hot-melt adhesive. The application of adhesive takes place in points, in a grid, in strips that run in lines crosswise to the elongation direction, or over the full area. The hot-melt adhesives used are preferably elastic thermoplastics on the basis of SIS, SBS, or SEBS polymers or mixtures of them. The hot-melt adhesive is preferably applied at weights per surface area unit between 2 g/m² and 20 g/m², between the elastic carrier film and the cover layer. If the hot-melt adhesive is applied in lines, the distance between lines of adhesive can amount to 0.2 mm to 5 mm, preferably 0.5 mm to 2 mm. The width of the track of adhesive preferably amounts to 0.3 mm to 2 mm, particularly preferably 0.5 mm to 1.5 mm.

The invention also includes a method for applying the laminate material.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIGS. 2a and 2b show a filament from which the cover layer of the laminate material is produced;

DETAILED DESCRIPTION OF THE PREFERRED EMBODIMENT

Figure 1A:
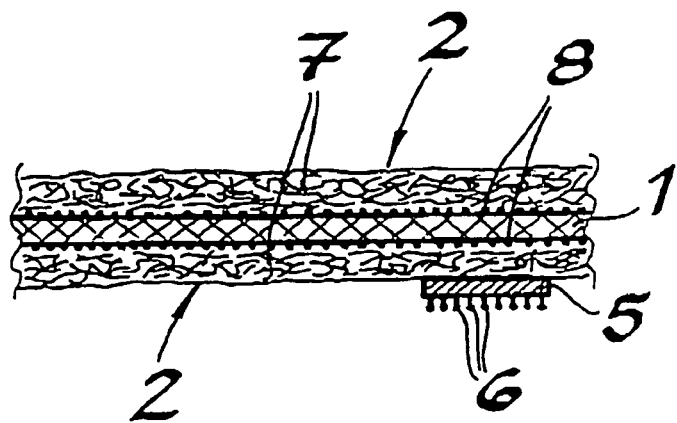
FIGS. 1a and 1b show a laminate material according to the invention, in the non-stretched as well as in the stretched state.
Figure 1B:
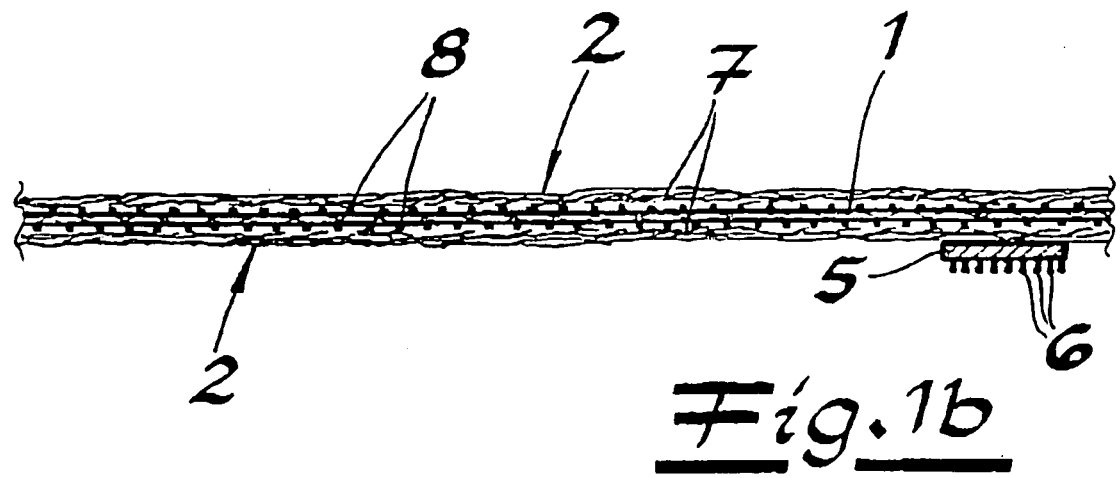

FIGS. 1a and 1b show a laminate material for an elastic diaper closure consisting of an elastic carrier film 1, which has a preferred elongation direction, and two cover layers 2 laminated on, made of a fiber non-woven fabric, which contains fibers 3 of an elastic polymer and fiber components 4 of a non-elastic thermoplastic polymer, which have been stretched in the preferred elongation direction by stretching the fiber non-woven fabric 2. On the outside of one cover layer 2, a hook tape 5 having male closure elements 6 is attached, which form a hook and loop closure together with female closure elements that are glued on in the front waistband region of a diaper, not shown. A comparison of FIGS. 1a and 1b shows that the laminate material can be elastically stretched in the preferred elongation direction shown. The laminate material allows an elastic lengthening by 30% to 150% of the original length. A steep increase in force defines that the elastic elongation limit has been reached.

Figure 3:
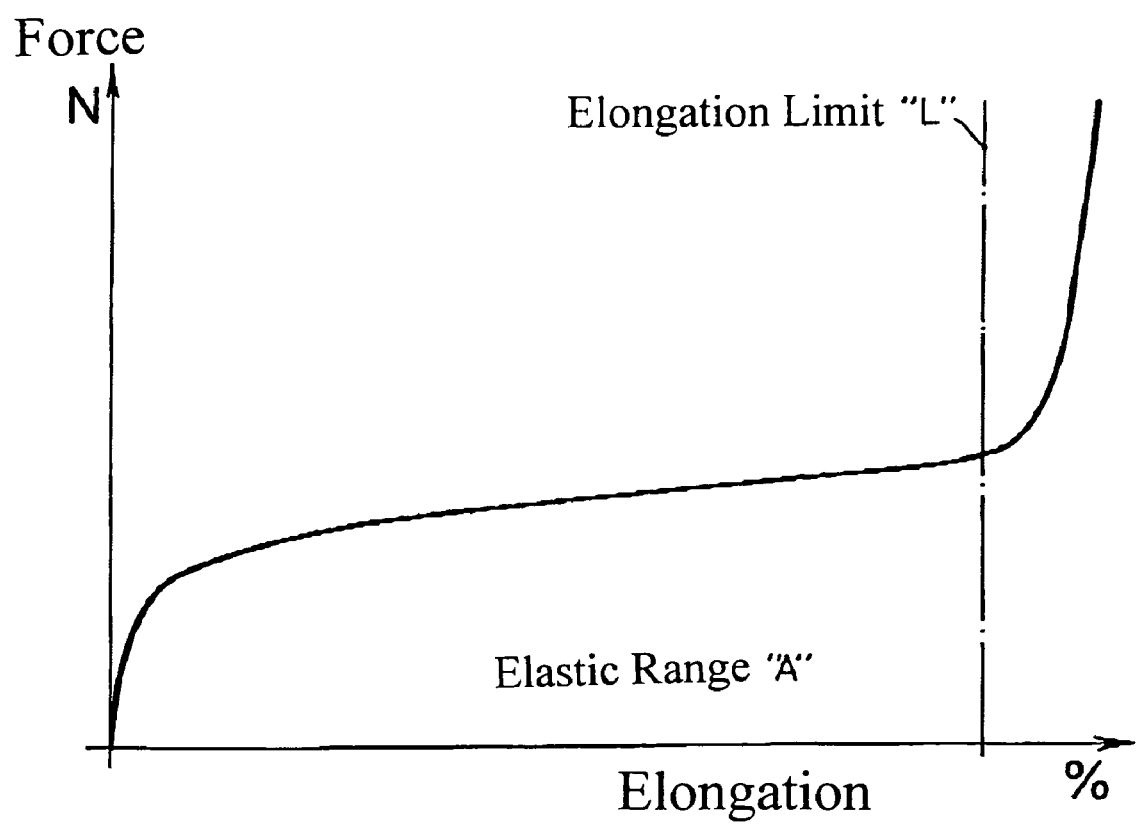
FIG. 3 shows an elongation/tension diagram of the laminate material.

The elongation behavior of the material is shown in FIG. 3. In FIG. 3, the tensile force required to stretch the laminate material according to the invention is plotted above the elongation (lengthening with reference to the original length). As shown in FIG. 3, the laminate material can be stretched with little force up to the elongation limit. Over this elongation range, the laminate material exhibits elastic recovery when the stress is relieved. When the elongation limit that has been established in the material is reached, a great increase in the force required for further stretching is observed. This range is clearly perceived as a non-elastic range.

In the exemplary embodiment, the cover layer consists of a spun-bonded fabric, the filaments 7 of which have a filament core 3 of a thermoplastic elastomer, and a filament mantle 4 of a non-elastic thermoplastic polymer. The fiber non-woven fabric 2 is modified by means of pre-stretching, before it is laminated onto the carrier film 1. The structure of the filaments changes as a result of the pre-elongation or pre-stretching. This becomes clear from a comparison of FIGS. 2a and 2b. Before pre-stretching, filaments 7 of the fiber non-woven fabric 2 have the geometry shown in FIG. 2a. Filament mantle 4 is plastically deformed as a result of the pre-stretching of the fiber non-woven fabric, while the filament core 3 merely undergoes elastic deformation. After pre-stretching, filament 7 contracts again, and then possesses the contour shown in FIG. 2b. Because of the plastic deformation of non-elastic filament mantle 4, the latter now possesses a wavy structure. If filament 7 is stretched in use, the non-elastic filament mantle 4 at first aligns along the elastic filament core 3 and exerts practically no resistance to stretching.

Once filament 7 has reached a non-wavy contour again as the result of stretching, which contour essentially corresponds to the representation in FIG. 2a, the elastic elongation limit of the fiber non-woven fabric 2 has been reached, and stretching beyond this elongation limit can only take place if filament mantle 4 experiences further cold stretching. This second cold stretching is connected with a steep increase in the force required for further stretching. In this range, fiber non-woven fabric 2 therefore no longer demonstrates any elastic properties. This becomes particularly clear from FIG. 3, in which the tensile force required to stretch a laminate material according to the invention is plotted over the elongation. In the non-stretched state, filaments 7 of the laminate material have the contour shown in FIG. 2b. In the elastic elongation range "A," the curve runs relatively flat over a large range, so that only comparatively slight forces are required to stretch the laminate material in this range. When the upper limit of the elastic range has been reached, filaments 7 possess a contour that they also possessed during the maximal elongation during pre-stretching. In the case of stretching beyond elastic elongation limit "L," the force required for this increases steeply upward, and this is accompanied by further cold-stretching of non-elastic filament mantle 4. Therefore, the size of elastic range "A" can be adjusted, in targeted manner, by the pre-stretching of filaments 7. Fiber non-woven fabric 2 may consist of a fiber mixture of elastic fibers and fibers of a non-elastic thermoplastic polymer.

To produce the laminate material according to the invention, a web of fiber non-woven fabric is first produced, which contains elastic fibers and fiber components of a non-elastic thermoplastic elastomer. This web is subsequently stretched in its crosswise direction, stretching the non-elastic fiber components. For this crosswise stretching, the fiber non-woven fabric 2 is passed over a stretching frame or through a roller arrangement of profiled rollers, e.g. grooved rollers, for example. This results in stretching in the crosswise direction of the web, by 50% to 200% of the original web width, whereby the crosswise elongation is coordinated with the desired elongation limit of the laminate material. The stretched fiber non-woven fabric 2 recovers elastically after the crosswise stretching has taken place, and essentially goes back to its initial width.

The fiber non-woven fabric 2 that has been modified by means of pre-stretching is laminated onto the carrier film 1, using an elastic hot-melt adhesive 8. The hot-melt adhesive 8 can be applied in strips parallel to the lengthwise direction of the web. The strips have a width of preferably 0.3 to 2 mm, particularly preferably 0.5 to 1.5 mm, and are applied to the elastic carrier film 1 and/or the non-woven fabric web at a spacing of 0.2 to 5 mm, preferably 0.5 to 2 mm.

Elastic adhesive 8 can contain SIS, SBS, SEBS, or PU polymers or mixtures of them. It is practical if adhesive 8 is applied to fiber non-woven fabric 2 and/or carrier film 1 at an application weight of 5 to 10 g/m2. Adhesive 8 can also be sprayed onto the entire area, thereby producing a closed adhesive film or an open, discontinuous, scaly adhesive film.

Fiber non-woven fabric 2, i.e. the fiber non-woven fabrics 2 and carrier film 1, are pressed together in a lamination unit, by means of two rollers. The laminate material produced according to this method is resistant to tension in the lengthwise direction, and behaves non-elastically in the lengthwise direction of the web. In the crosswise direction, however, the laminate material behaves with almost the elasticity of rubber, up to the elongation limit that has been established according to the invention. In other words, the laminate material returns to its original position after being stretched. The laminate material that has been glued in this manner is cut to the width of the finished product. For use in diaper closures, the elastic laminate material is supplemented with hook tapes 5, self-adhesive coating masses, and non-adhesive films, and processed into rolls. The laminate material preferably allows an elongation and elastic recovery of 30 to 150%, whereby the steep increase in force defines that the elastic elongation limit has been reached.

Accordingly, while only a few embodiments of the present invention have been shown and described, it is obvious that many changes and modifications may be made thereunto without departing from the spirit and scope of the invention.

What is claimed is:

1. A tape for diaper closures, comprising
   an elastic carrier film that has a preferred elongation direction and comprises a multi-layer co-extrusion film with a core of a thermoplastic elastomer and an adhesion-imparting layer,
   at least one cover layer that is laminated on the elastic carrier film, the cover layer comprising a spun-bonded fabric having filaments, said filaments having a filament core of a thermoplastic elastomer, and a filament mantle of a non-elastic thermoplastic polymer that has been deformed as a result of pre-stretching, and
   a hook tape having male closure elements, said hook tape being attached to the cover layer by gluing or bonding and forming a hook and loop closure with female closure elements that are attached on a front waistband of a diaper,
   wherein the non-elastic thermoplastic elastomer within the filaments is 20-60 wt-% of the total weight of the fabric, and wherein the fabric has a defined elongation limit resulting from pre-stretching in the preferred elongation direction by means of an elongation of the fabric;
   and wherein the carrier film and the cover layer are connected by an elastic hot melt adhesive that is applied in points, in a grid or in strips that run in lines crosswise to the elongation direction.

2. Laminate material as recited in claim 1, wherein the cover layer has a weight per surface area unit between 10 g/m$^2$ and 200 g/m$^2$.

3. Laminate material as recited in claim 1, wherein the elastic carrier film has a weight per surface area unit between 5 g/m$^2$ and 150 g/m$^2$.

* * * * *